(12) United States Patent
Douglas et al.

(10) Patent No.: US 8,024,030 B2
(45) Date of Patent: Sep. 20, 2011

(54) SYSTEM AND METHOD FOR ANALYZING AN ELECTROCARDIOGRAM SIGNAL

(75) Inventors: Antony Louis Piriyakumar Douglas, Bangalore (IN); Wiebke Schulleri, Althengstett (DE)

(73) Assignee: Siemens Aktiengesellschaft, Munich (DE)

( * ) Notice: Subject to any disclaimer, the term of this patent is extended or adjusted under 35 U.S.C. 154(b) by 231 days.

(21) Appl. No.: 12/539,781

(22) Filed: Aug. 12, 2009

(65) Prior Publication Data

US 2011/0040200 A1 Feb. 17, 2011

(51) Int. Cl.
*A61B 5/04* (2006.01)
(52) U.S. Cl. ....................................... 600/517
(58) Field of Classification Search .................. 600/517
See application file for complete search history.

(56) References Cited

U.S. PATENT DOCUMENTS

| | | | |
|---|---|---|---|
| 4,930,075 | A | 5/1990 | Kortas |
| 5,323,783 | A | 6/1994 | Henkin |
| 6,381,493 | B1 * | 4/2002 | Stadler et al. ................. 607/9 |

FOREIGN PATENT DOCUMENTS

| DE | 202006016182 U1 | 1/2007 |
|---|---|---|
| EP | 0545628 A2 | 6/1993 |

* cited by examiner

*Primary Examiner* — George Manuel

(57) ABSTRACT

A system for analyzing an ECG signal is provided. The system comprises an interface that receives an ECG waveform associated with heart beat cycle of a patient. The system includes signal processor that determines a first isoelectric portion lying between a T-wave of a first heart beat cycle and a P-wave of a successive heart beat cycle, and a second isoelectric portion lying between a P-wave and a QRS complex of the first heart beat cycle. The signal processor determines a stability measure for each of said first and second portions and adaptively selects the first or the second portion as a baseline for the first heart beat cycle based on the stability measures. The signal processor determines a point of reference on an ST segment associated with the first heart beat cycle and evaluates a deviation of the point of reference on the ST segment from the selected baseline.

20 Claims, 10 Drawing Sheets

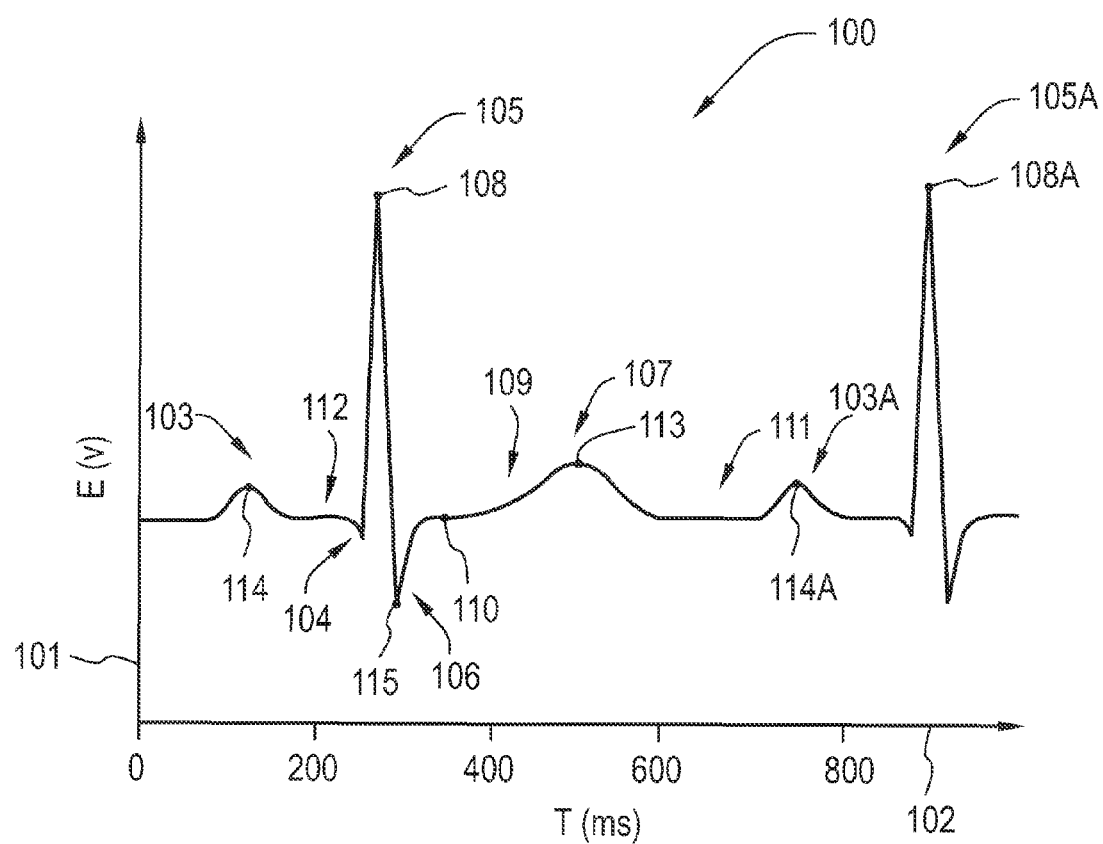
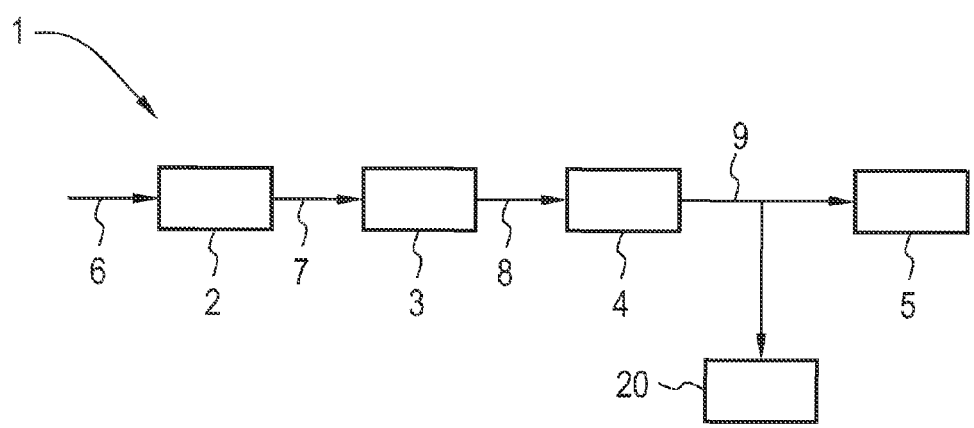

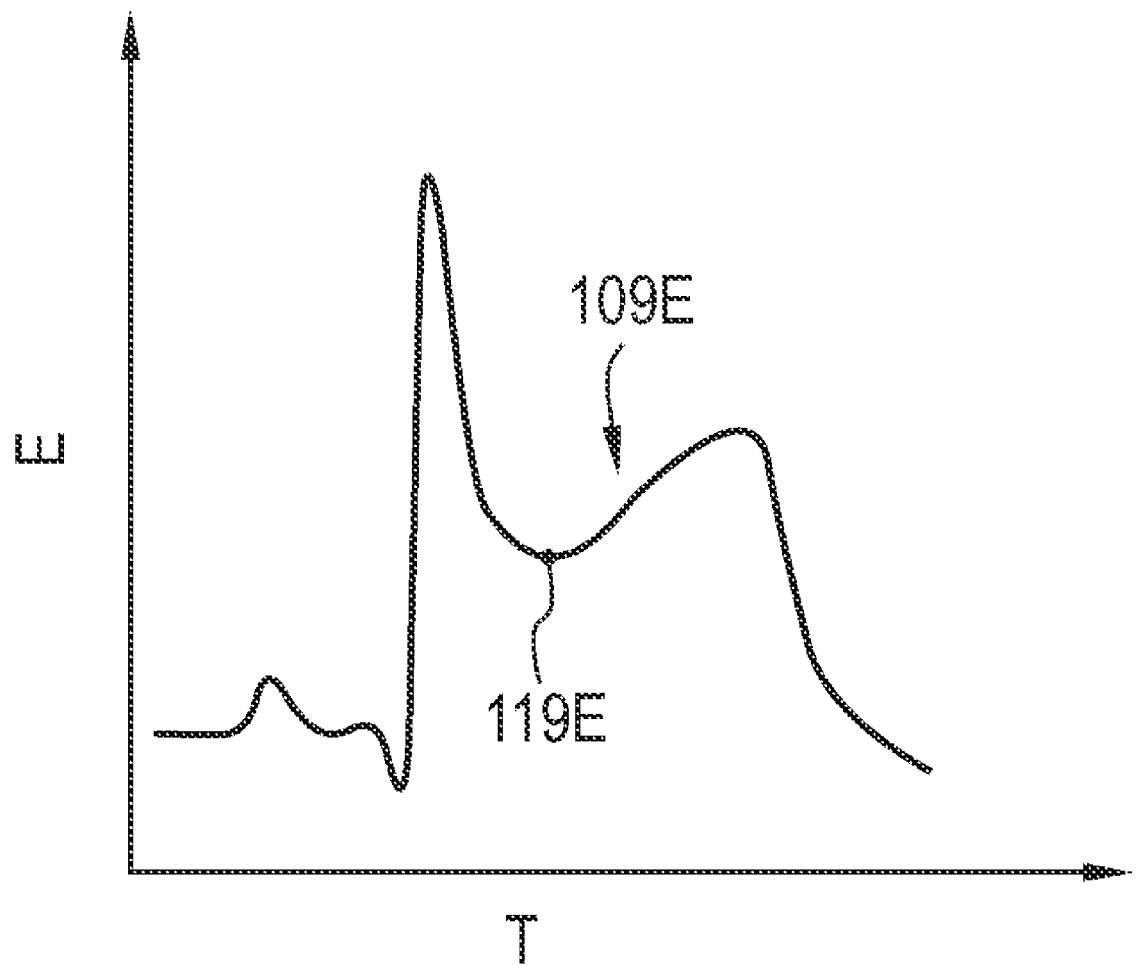

SYSTEM AND METHOD FOR ANALYZING AN ELECTROCARDIOGRAM SIGNAL

FIELD OF INVENTION

The present invention relates to a system and method for analyzing an electrocardiogram (ECG) signal, in particular, for estimating an ST segment deviation for evaluating a medical condition of a patient.

BACKGROUND OF INVENTION

Electrocardiography is the recording of the electrical activity of the heart over time via skin electrodes. An electrocardiogram (ECG) is used by cardiologists to aid in the diagnosis of various cardiac abnormalities. Cardiac arrhythmia and ischemia are some of the conditions that are identified through the analysis of ECG. There is a strong correlation between the ST segment deviation and the incidence of ischemia and thus ST segment deviation measurement is an important parameter in clinical study. Further, morphology of the ST segment is an important clinical parameter in identifying a type of heart attack. Some of these types of heart attacks are ST Elevation Myocardial Infarction (STEMI) and Non ST Elevation Myocardial Infarction (NSTEMI) which can be identified through ST segment morphology. Further, the shape/geometry of the ST morphology can also be used as an indicator of an impending heart attack and also to understand the severity of the occurred heart attack.

However, automated measurement of ST segment deviation and classification of ST segment morphology presents technical difficulties like the presence of noise in the signal, baseline wander of the signal and so on.

Accordingly, there is a need for a robust technique of automated ST segment deviation computation.

SUMMARY OF INVENTION

Briefly, in accordance with one aspect of the present invention, a system for analyzing an electrocardiogram (ECG) signal comprises an interface that receives and digitizes an ECG signal waveform associated with a series of heart beat cycles of a patient and a signal processor that processes digitized data samples representing the ECG waveform to evaluate an ST segment deviation. To determine ST segment deviation the signal processor determines a first and a second isoelectric portion of the ECG waveform, the first isoelectric portion lying temporally between a T-wave of a first heart beat cycle and a P-wave of a successive heart beat cycle, the second isoelectric portion lying temporally between a P-wave of the first heart beat cycle and a QRS complex of the first heart beat cycle. The signal processor further determines a stability measure for each of said first and second isoelectric portions. The signal processor adaptively selects the first isoelectric portion or the second isoelectric portion as a baseline for the first heart beat cycle based on the stability measures of the first and second isoelectric portions. The signal processor further determines a point of reference on an ST segment on the ECG waveform associated with the first heart beat cycle and evaluates a deviation of the determined point of reference on the ST segment from the selected baseline.

In accordance another aspect of the present invention, a method for analyzing an electrocardiogram (ECG) comprises providing digitized data samples of an ECG waveform associated with a plurality of heart beat cycles of a patient. The method then includes determining a first isoelectric portion of said ECG waveform from data samples of said ECG waveform between a T-wave of a first heart beat cycle and a P-wave of a successive heart beat cycle and a second isoelectric portion of said ECG waveform from data samples of said ECG signal waveform between P-wave of the first heart beat cycle and a QRS complex of the first heart beat cycle. The method further comprises determining a stability measure for each of said first and second isoelectric portions and adaptively selecting the first isoelectric portion or the second isoelectric portion as a baseline for the first heart beat cycle based on a comparison of the stability measures of said first and second isoelectric portions. Still further, the method comprises determining a point of reference on an ST segment of the ECG waveform associated with the first heart beat cycle and evaluating a deviation of the point of reference with respect to the selected baseline.

In accordance with yet another aspect, a method for aiding diagnosis of a medical condition a patient from an electrocardiogram (ECG), comprises providing digitized data samples of an ECG waveform associated with a plurality of heart beat cycles of the patient. The method further includes adaptively selecting a baseline for a first heart beat cycle between a first isoelectric portion of said ECG waveform lying temporally between a T-wave of the first heart beat cycle and a P-wave of a successive heart beat cycle and a second isoelectric portion lying temporally between P-wave of the first heart beat cycle and a QRS complex of the first heart beat cycle. The adaptive selection being based on a stability measure determined for each of said first and second isoelectric portions. Further, the method includes evaluating a deviation of a J-point on an ST segment associated with the first heart beat cycle with respect to the selected baseline. The method subsequently includes classifying the ST segment into one of a plurality of morphological classes based on the determined deviation of the J-point from the selected baseline.

BRIEF DESCRIPTION OF THE DRAWINGS

The present invention is further described hereinafter with reference to exemplary embodiments shown in the accompanying drawings, in which:

FIG. 1 is an exemplary ECG plot,

FIG. 2 illustrates a system for analyzing an ECG signal according to one embodiment of the present invention, FIGS. 9A-9E are graphical illustrations of various ST segment morphologies.

DETAILED DESCRIPTION OF INVENTION

Figure 3:
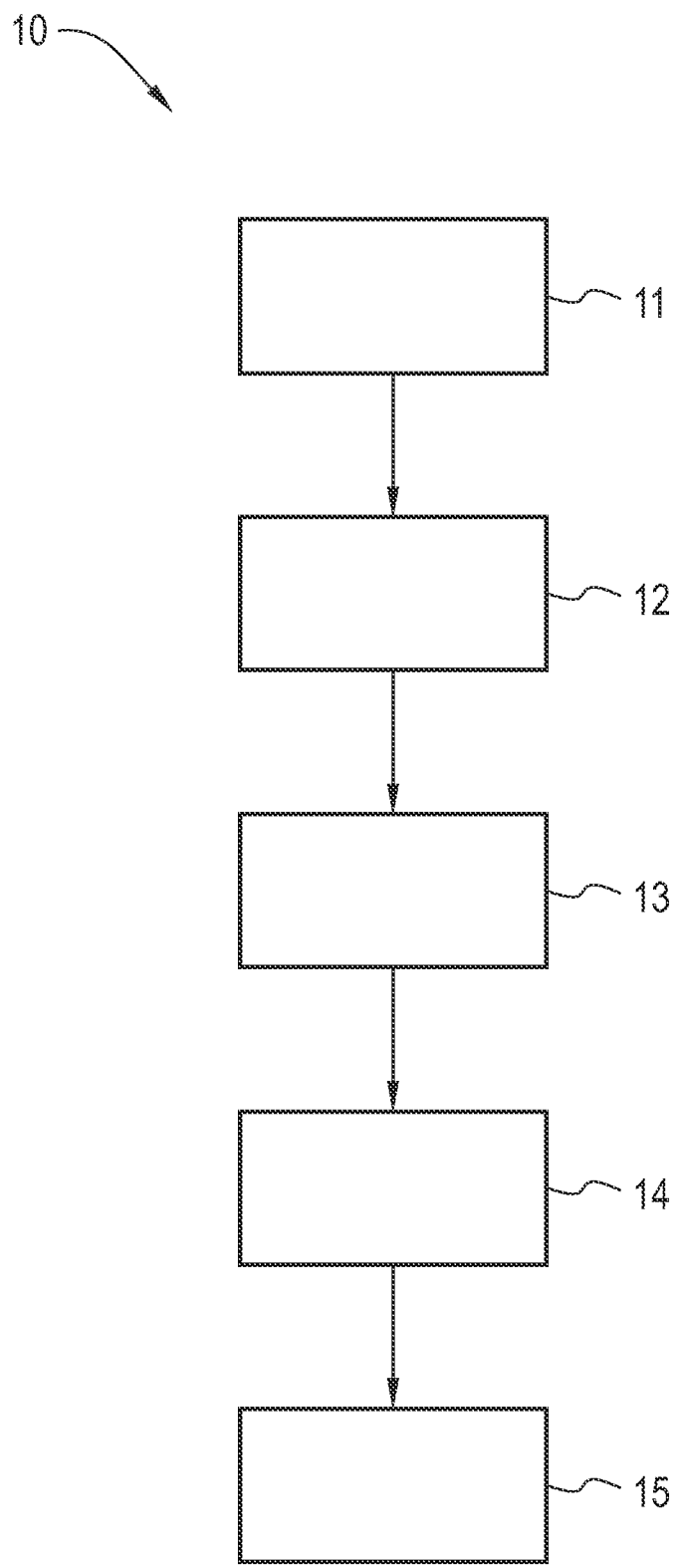
FIG. 3 is a high level flowchart illustrating an exemplary method for analyzing an electrocardiogram to evaluate ST segment deviation.

FIG. 1 shows an exemplary plot 100 representative of human ECG waveform, wherein the axis 101 represents an electrical voltage (V) associated with heart electrical activity of a patient as measured by an ECG electrode and the axis 102 represents time (ms). A deflection 103 is known as a "P-wave" and is a resultant of excitation of the atria of the heart. Deflections 104, 105 and 106 are known as "Q-wave," "R-wave," and "S-wave" respectively. The Q-wave, R-wave and S-wave in the ECG waveform result from excitation (de-polarization) of the ventricles of the heart and are hence collectively referred to as a QRS complex. It should be noted that not every QRS complex contains a Q-wave, an R-wave, and an S-wave. By convention, any combination of these waves can be referred to as a QRS complex. Deflection 107 is known as a "T-wave" and is a resultant of recovery (repolarization) of the ventricles. The temporal distance on the ECG waveform from the peak point 108 of a first R-wave 105 to the peak point 108A of a next R-wave 105A is known as an R-R or inter-beat interval. The time duration of the R-R interval referred to as a cardiac cycle or a heart beat cycle.

The portion 109 of ECG 100 between the end of the S-wave 106 and the beginning of T-wave 107 is known as an ST segment. A point 110, referred to as a J-point, marks the end of the QRS complex and is used to indicate the beginning of ST segment 109. The portion 111 of ECG waveform between the end of T-wave 107 of one heart beat cycle and the beginning of P-wave 103A of the successive heart beat cycle is referred to as a TP segment. The portion 112 of ECG waveform between the end of P-wave 103 and the beginning of the QRS segment is referred to as a PQ segment. The TP and PQ segments include generally isoelectric (i.e., flat) portions of the ECG resulting from insignificant heart electrical activity during such time intervals.

Measurement of ST segment deviation measurement is an important parameter in clinical study since there is strong correlation between the ST segment deviation and the incidence of cardiac abnormalities like myocardial ischemia and myocardial infarction. Embodiments of the present invention provide a robust solution for automated measurement of ST segment deviation and classification by a beat by beat evaluation of ST segment deviation with respect to a baseline that is adaptively selected between isoelectric portions of the TP segment and PQ segment based on a stability measure of these isoelectric portions. Embodiments of the present invention are described in greater detail herein below.

FIG. 2 is a block diagram of a system 1 for analyzing an ECG signal in accordance with one embodiment of the present invention. The system 1 comprises an interface 2 that receives a signal 6 associated with an electrocardiogram of a patient for a series of heart beat cycles. The signal 6, which is referred to herein as an ECG signal, may comprise a digitized or analog signal representative of the patient ECG and may be received directly from ECG electrodes coupled to the patient or may be transmitted remotely from the ECG electrodes via any intermediate means. The signal 6 has an ECG waveform associated with heart electrical activity of the patient. If not already digitized, the interface 2 digitizes the signal 6 to provide digitized data samples 7 of the ECG for further processing. A signal pre-processor 3 may be optionally provided for filtering the digitized data samples. Filtering of the ECG data may involve one or more of low pass filtering the ECG data to remove high frequency noise, applying a baseline wander removal filter to the ECG data to remove low frequency artifacts, removing ventricular arrhythmias from the ECG data, and eliminating noisy beats from the ECG data.

The filtered data samples 8 are analyzed by a signal processor 4 to perform a beat by beat evaluation of ST segment deviation using an adaptively selected baseline and for morphological classification of the ST segments as explained in detail hereinafter. Based on the output 9 of the signal processor 4, a diagnostic module 5 evaluates a medical condition of the patient, which may include, for example, determining the existence and/or gradation of cardiac abnormalities such as myocardial ischemia, myocardial infarction, among others. The output 9 of the signal processor may further be communicated to a user interface (UI) 20. The UI 20 comprises, for example, one or more display images generated by a user interface processor and enabling user interaction with a processor or other device and associated data acquisition and processing functions.

A "processor" as used herein is a device for executing machine-readable instructions stored on a computer readable medium, for performing tasks and may comprise any one or combination of, hardware and firmware. A processor may also comprise memory storing machine readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

The UI 20 also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

FIG. 3 is a high level flowchart illustrating an exemplary method 10 for analyzing an electrocardiogram. Activities or steps of the method 10 may be performed, for example, by one or more processors of the type illustrated above. The method 10 begins at block 11 by receiving digitized data samples representing a patient ECG waveform over a series of heart beat cycles. These data samples may be provided remotely or otherwise in response to an electrocardiography performed on the patient. Optionally, at block 12, these data samples are filtered to make them more suitable for subsequent processing. Block 13 involves adaptively determining a baseline beat-by-beat, for each heart beat cycle. As described in greater detail referring to FIG. 4, the baseline determined at block 13 is adaptively selected from a first isoelectric portion lying temporally between the T-wave of one heart beat cycle and a P-wave of the next heart beat cycle (i.e., including the TP segment) and a second isoelectric portion lying temporally between the P-wave of one heart beat cycle and the QRS complex of that heart beat cycle (i.e., including the PQ segment) in the ECG waveform based on a stability measure determined for each of these isoelectric portions. At block 14, a point of reference is identified on an ST segment of each beat which is used to measure the ST deviation. As used herein, the point of reference refers to a representative point on the ST segment that best characterizes the deviation (i.e., elevation or depression) of the ST segment from the baseline. As described in greater detail referring to FIG. 7, the point of reference may be taken to be a J-point determined on the ST segment, or may be temporally displaced from the J-point. For increased accuracy in measuring ST deviation, the temporal distance of the point of reference from the J-point is determined based on the morphological classification of the ST segment. As used herein, temporal distance between two points in an ECG waveform refers to a time interval between the occurrences of those two points in the ECG waveform. Referring back to FIG. 3, at block 15 of the method 10, a deviation (i.e., elevation or depression) of the point of reference from the baseline is evaluated, which may be subsequently used, for example for diagnosing a heart abnormality and/or a gradation thereof.

As used herein, deviation of a point from the baseline refers to a difference in the value of the data sample associated with that point with a value associated with the baseline. The value associated with the baseline may be determined for example as a mode, median or mean of values of the data samples representing the baseline. Further, as used herein, the value of a data sample is indicative of an electrical voltage corresponding to the point in the ECG waveform represented by the data sample. Hence, in other words, deviation of a point from a baseline is a measure of the difference in the electrical voltage corresponding to that point on the ECG waveform and the electrical voltage associated with the baseline.

Figure 4:
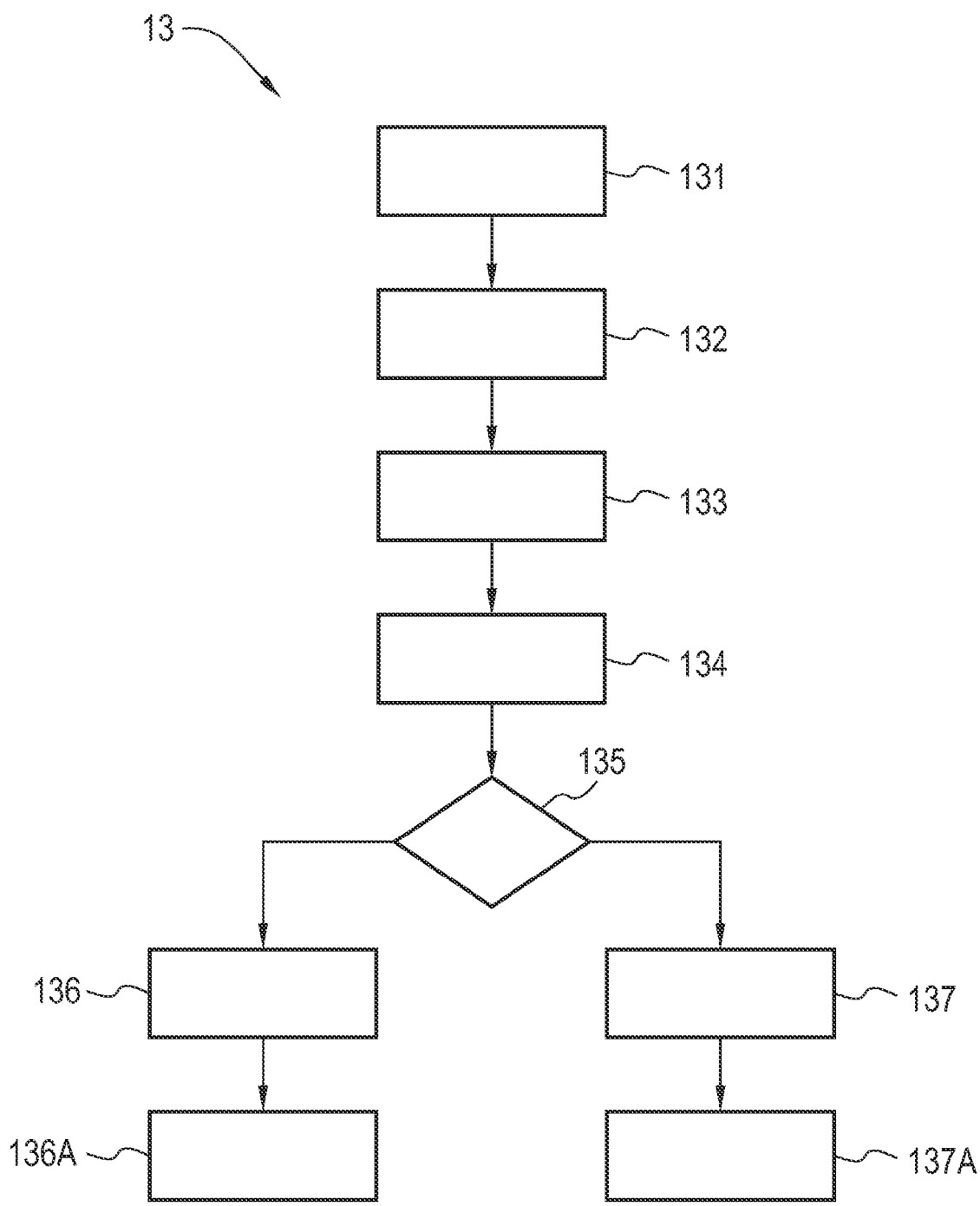
FIG. 4 is a flowchart illustrating an exemplary method for adaptive determining the baseline for a heart beat cycle.

Referring to FIG. 4 is illustrated an exemplary embodiment of a method 13 for adaptively determining a baseline for a heart beat cycle from the digitized ECG data samples. Activities or steps of the method 13 may be performed, for example, by one or more processors of the type illustrated above. As isoelectric portion in an ECG waveform is a generally flat portion of the ECG that corresponds to quiet period of the heart electric activity. In practice however, an isoelectric portion may not be exactly flat and may have some variation in slope. Hence, as used herein, an isoelectric portion referrers to a substantially flat portion of the ECG represented by a series of data samples whose slope changes lie within a threshold value. The threshold value may be a predetermined value based on the degree of accuracy sought. The method 13, first involves determination of fiducial points on the ECG including an R-peak, a T-peak and a P-peak (block 131). These fiducial points are determined for successive heart beat cycles. An R-peak, represented by the point 108 in FIG. 1, refers to the peak point of the R-wave 105. The R-peak may be determined as the maximum value of the ECG data in a heart beat cycle. There are several known techniques to determine an R-peak and products are currently available in the market that are able to detect an R-peak with high degrees of accuracy. Once the R-peak is known, the other fiducial points are determined, for example as described below.

In the illustrated embodiment, the T-peak of a heart beat cycle is determined as the peak point in the ECG waveform that lies temporally between R+x and R+y, wherein R is the temporal location of the R-peak, and x and y are temporal distances in milliseconds (ms) from the R-peak and determined based on heart rate (HR), wherein x=60 ms and y=200 ms for HR>120 beats per minute, and x=80 ms and y=300 ms for HR<=120 beats per minute In the illustrated embodiment, the P-peak of a heart beat cycle is determined as the peak point in the ECG waveform that lies temporally between R−x and R−y, wherein R is the temporal location of the R-peak, and x and y are temporal distances in milliseconds (ms) from the R-peak and determined based on heart rate (HR), wherein x=60 ms and y=160 ms for HR>120 beats per minute, and x=80 ms and y=200 ms for HR<=120 beats per minute Block 132 involves determining the first isoelectric portion by processing the data samples between the T-peak of one heart beat cycle and the P-peak of the next heart beat cycle, which may have been determined, for example as described above. The first isoelectric portion may be identified as a length of data samples between the aforementioned T-peak and P-peak whose slope change (i.e., derivative) is lesser than a threshold value. The region between the T-peak and P-peak that qualifies as an isoelectric portion shows insignificant slope change and is hence difficult to detect. Hence an advantageous embodiment of determining the first isoelectric portion involves determining exponential values of data samples of the digitized ECG waveform lying between the aforementioned T-peak and P-peak. The exponents of the data samples are determined to advantageously exaggerate the slope change and hence an exponential function advantageously creates a closer grouping of the flattest segment. A derivative value (indicating slope change) is then determined for the exponential values for each of these data samples and a series of data samples are identified whose derivative (slope change) is less than a threshold value (for example 0.05). The first isoelectric portion is determined as a portion of the ECG waveform that is represented by a length of such identified series of data samples. The above technique thus ensures higher degree of stability for the identified isoelectric portion. However, the technique mentioned above is exemplary and the first isoelectric portion may alternately be determined using any other technique.

Block 133 involves the determination of the second isoelectric portion by processing the data samples between the P-peak and peak of the QRS complex (i.e., the R-peak) of the heart beat cycle. The second isoelectric portion may be identified as a length of data samples between the aforementioned P-peak and R-peak whose slope change (i.e., derivative) is lesser than a threshold value. Advantageously, to obtain a stable set of data samples to represent the second isoelectric portion, the second isoelectric portion may be determined in a similar manner to the first isoelectric portion as described above by determining exponential values of data samples lying between the aforementioned P-peak and R-peak, determining a derivative value (indicating slope change) for the exponential values for each of these data samples and identifying a series of data samples are identified whose derivative (slope change) is less than a threshold value.

Block 134 involves determination of a stability measure for the first and second isoelectric portions. The stability of an isoelectric portion is affected by noise. To overcome the effect of noise, in one embodiment, the stability measures of the first and second isoelectric portions are determined based on the number of representative data samples for the respective isoelectric portions, i.e., higher the number of representative data samples in an isoelectric portion, greater is the stability measure determined for the isoelectric portion. Additional considerations may also be made in determination of the stability measures, including, for example, the standard deviation of the derivatives of the representative data samples from the isoelectric (horizontal) level, or a standard deviation of the derivatives of the exponentials of the representative data samples, depending on the amount of accuracy sought.

Figure 5:
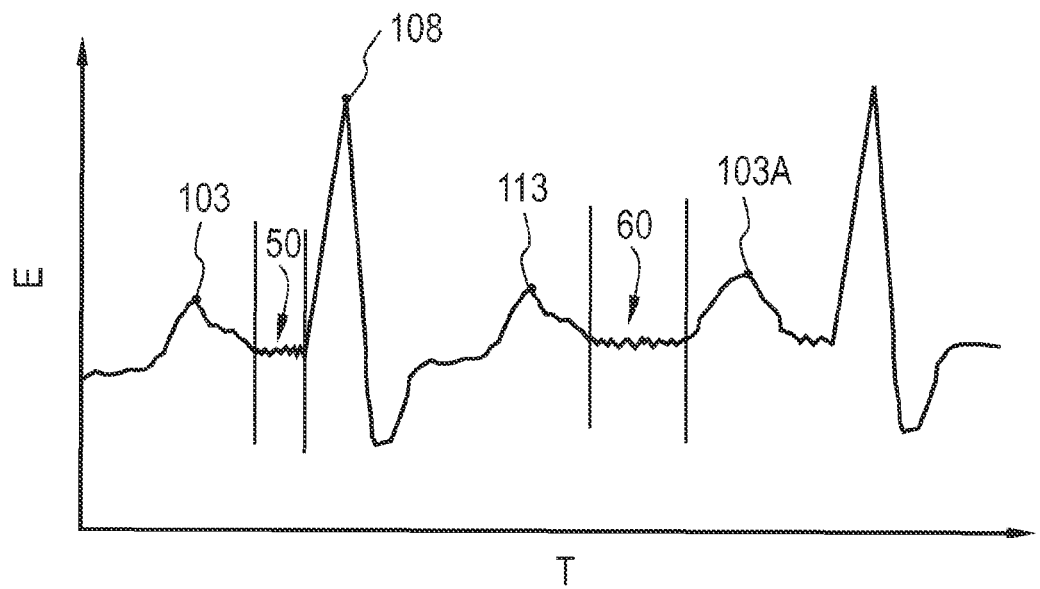
FIG. 5 illustrates the choice of baseline according to one example.
Figure 6:
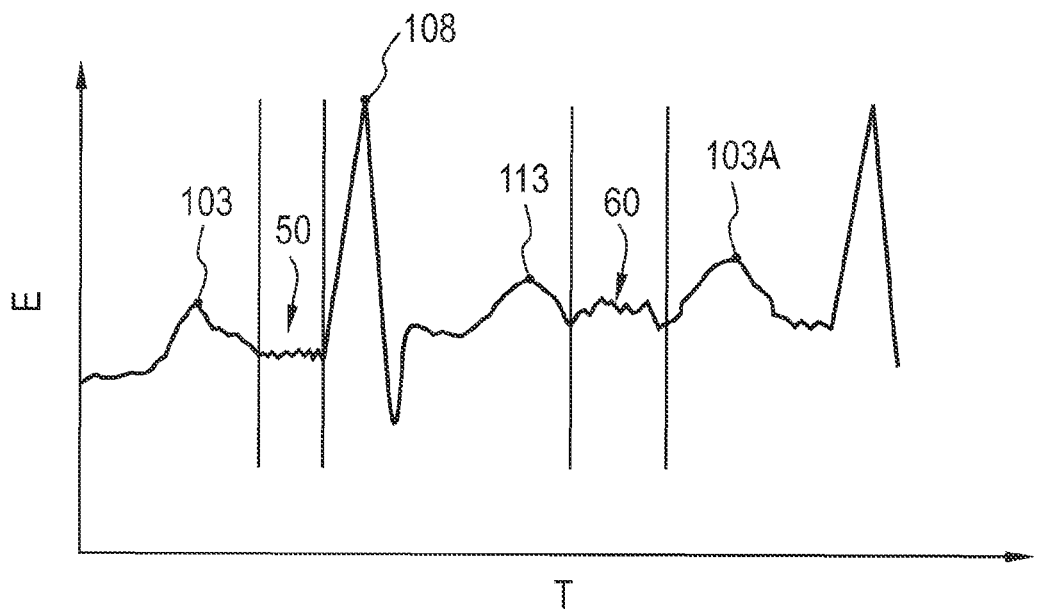
FIG. 6 illustrates the choice of baseline according to another example.

At block 135, a comparison is made between the stability measures of the first and second isoelectric portions. In response to the comparison at step 135, either the first isoelectric portion is selected (block 136) or the second isoelectric portion is selected (block 137) as the baseline for the heart beat cycle. Examples of adaptive selection of the baseline may be illustrated referring to FIG. 5 and FIG. 6, which show the first and second isoelectric portions represented by the portions 60 and 50 respectively on exemplary ECG waveforms. The first isoelectric portion 60 is located between T-peak 113 of one heart beat cycle and the P-peak of 103A of the next heart beat cycle. The second isoelectric portion 50 is located between the P-peak 103 and the R-peak 108 of the same heart beat cycle. In the example of FIG. 5, the first isoelectric portion 60 may be selected as the baseline for the heart beat cycle since it comprises a larger number of representative data samples than the second isoelectric portion 50, and hence posses a higher stability measure. In the example shown in FIG. 6, the second isoelectric portion 50 may be selected as the baseline over the first isoelectric portion 50 since the data samples of the second isoelectric portion 50 exhibit lesser slope variation than those of the first isoelectric portion 60 and hence posses a higher stability measure.

In accordance with the present invention, successive baselines are determined in an adaptive manner for successive heart beat cycles, which is used for a beat-by-beat evaluation of ST deviation as described below. Subsequently, at blocks 136A or 137A, the respective value associated with the baseline that is selected from the first or second isoelectric portion is determined. The value associated with the baseline may be determined for example as a mode, median or mean of values of the data samples representing the baseline.

Figure 7:
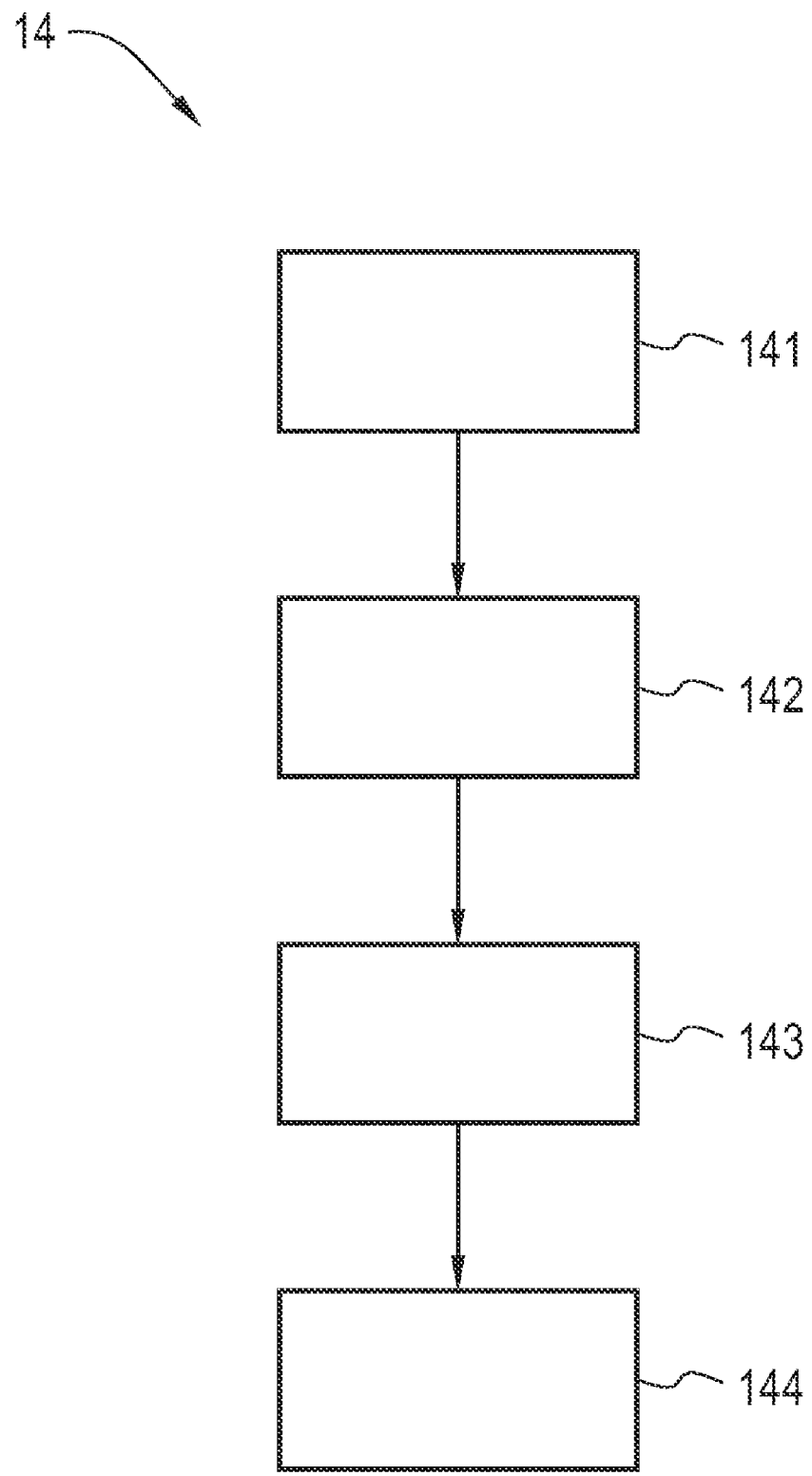
FIG. 7 is a flowchart illustrating an exemplary method for determining a point of reference on the ST segment, FIGS. 8A and 8B respectively illustrate determination of a J-point according to a first and second embodiment of the present invention.

Referring to FIG. 7 is illustrated an exemplary embodiment of a method 14 for determining a point of reference on an ST segment for measurement of ST deviation. Activities or steps of the method 14 may be performed, for example, by one or more processors of the type illustrated above. As mentioned the point of reference refers to a representative point on the ST segment that best characterizes the deviation (i.e., elevation or depression) of the ST segment from the baseline. In the illustrated embodiment, the point of reference is determined is response to determining a J-point (block 141) which marks the end of the QRS complex and the beginning of ST segment. The J-point is often difficult to locate as it appears as a small kink in the ECG waveform. Owing to the presence of noise that cannot be fully removed by filtering, there may be many such kinks in the region of an expected J-point making its detection difficult. Further some ECG signals have a prominent J-point at all. In such cases, a candidate point is designated as a J-point that best fits the possible location of a J-point. In the embodiments illustrated below, a J-point is determined based on locational properties of the J-point. However, the determination of the J-point at block 141 may incorporate any other technique.

Figure 8A:
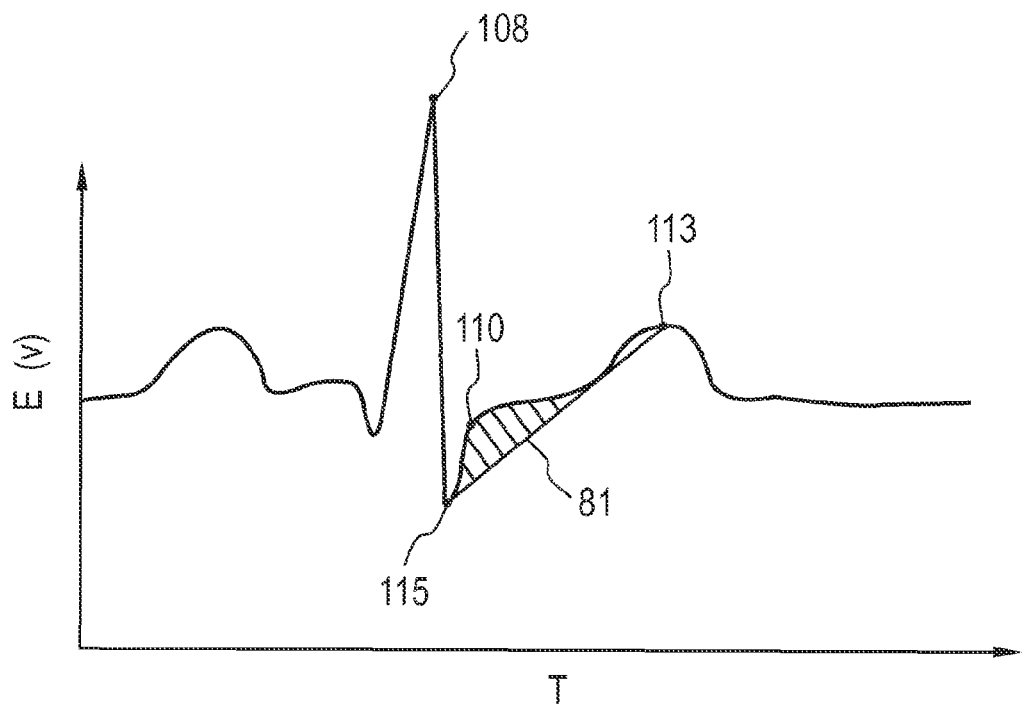
Figure 8B:
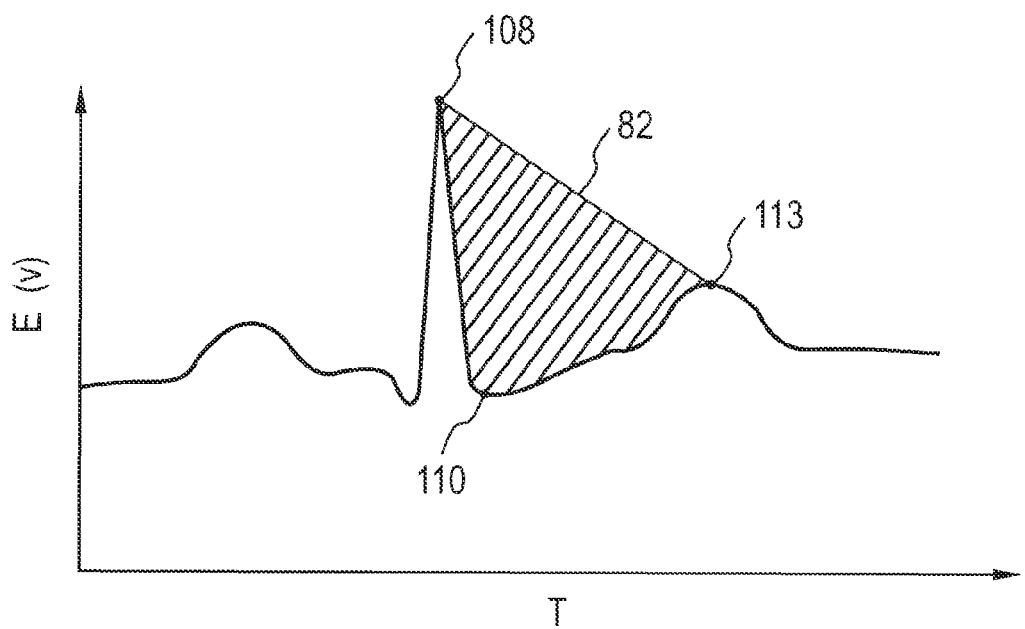
Figure 9A:
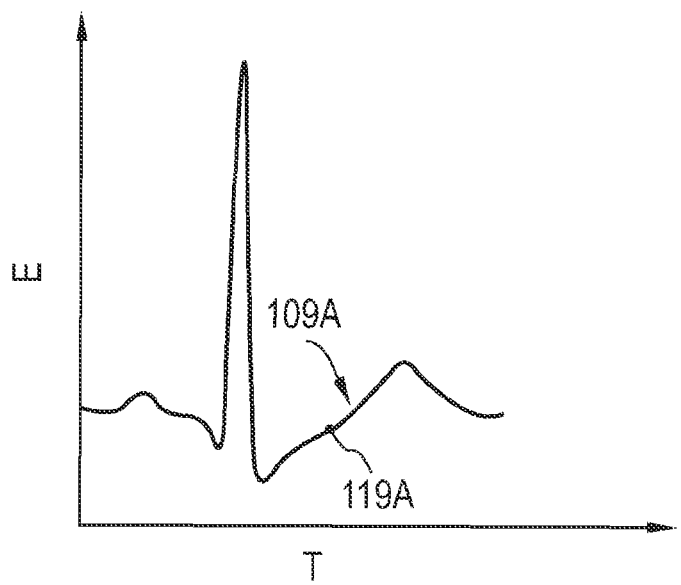
Figure 9B:
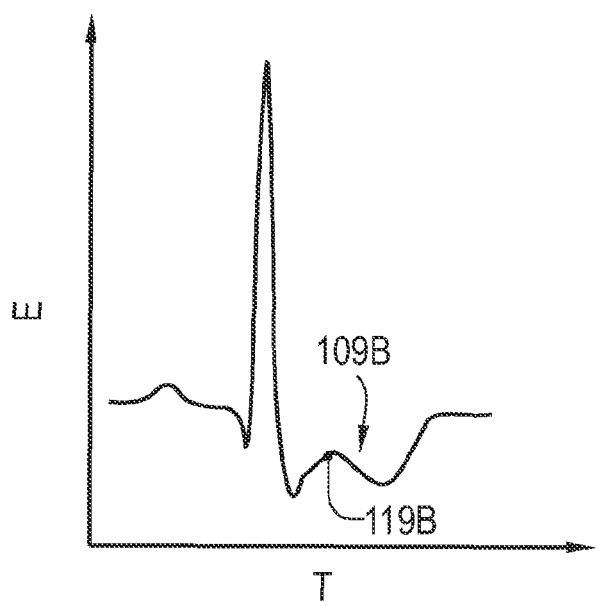
Figure 9C:
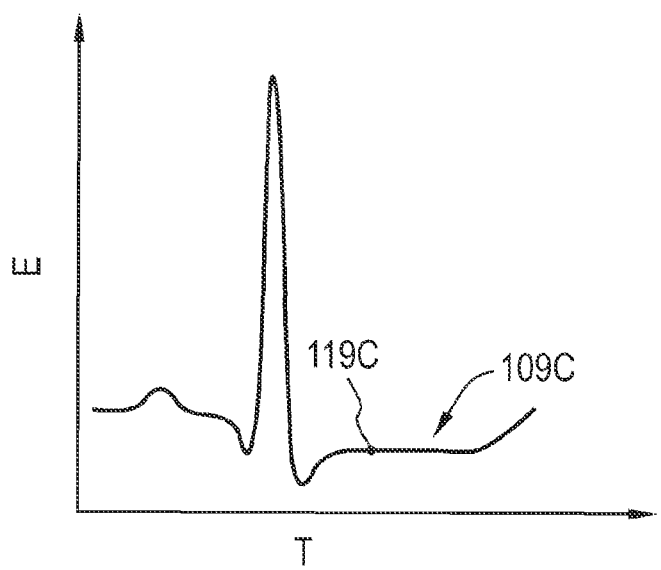
Figure 9D:
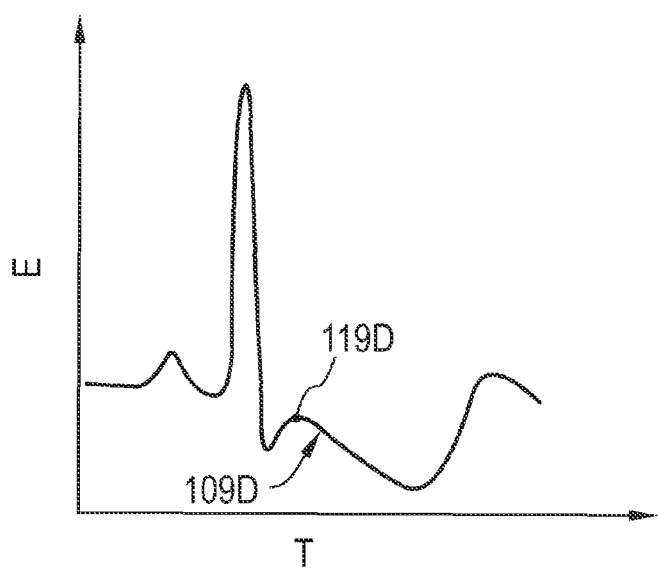

In one embodiment, the J-point is determined by first identifying an S-point and a T-peak. The S-point, represented by the point 115 in FIG. 1, may be determined as the first local minimum after the R-peak of the heart beat cycle. The S-point may be determined by several known techniques, including, for example, wavelet transforms. An exemplary determination of the T-peak from the R-peak has been described above. Referring to FIG. 8A, the J-point 110 may be determined as a point on the ECG waveform having maximum perpendicular distance from a line 81 between the S-point 115 and the T-peak 113. However, in some ECG waveforms, an S-point may not be distinctly identifiable. Accordingly, in an alternate embodiment as illustrated in FIG. 8B, the J-point 115 may be determined based on the R-peak 108 and the T-peak 113 without having to detect the S-point. Herein the J-point 110 may be determined as a point on the ECG waveform having maximum perpendicular distance from a line 82 between the R-peak 108 and the T-peak 113. Advantageously, a temporal property of the J-point that it should lie at round 40 ms from the R-peak may be additionally utilized to determine the J-point. Herein, candidate J-points are identified based on both the above described techniques and the J-point is determined as the one that lies at a temporal distance closest to 40 ms from the R-peak.

Referring back to FIG. 7, in one embodiment, the J-point determined at block 141 may taken as a point of reference for measuring ST deviation. However, in a preferred embodiment, for accurate evaluation of ST deviation, the point of reference is determined based on the exact morphological classification of the ST segment. The ST segment is classified by first evaluating (block 142) a deviation of the J-point from the baseline adaptively determined as described above. If the deviation is positive, i.e., if the value of the data sample representing the J-point is greater than the value associated with the baseline, the ST segment is classified as "elevation". The ST segment is classified as "depression" if the deviation is negative, i.e., if the value of the data sample representing the J-point is lesser than the value associated with the baseline. The exact morphological class of the ST segment is subsequently determined at block 143. In the illustrated example, the ST segment is classified into one of the following predetermined morphological classes including (a) upsloping depression, (b) convex depression, (c) horizontal depression, (d) downsloping depression and (e) elevation. These morphological classes of the ST segment are illustrated respectively in FIGS. 9A, 9B, 9C, 9D and 9E. Additionally, the classification may also include other morphological classes such as concave depression. Referring back to FIG. 7, in an exemplary embodiment, the classification at block 143 may include fitting a curve to a the portion of the ECG waveform after the J-point that includes the ST segment, applying a transform to the fitted curve to derive variance data indicating variance in the fitted curve and classifying the ST segment into one of the above mentioned morphological classes in response to the variance data. The transform may include, for example a Karhunen Loeve transform (KLT), or any other variance analysis transform. The curve that is fitted on to the ST segment may be selected to be a second degree curve or a first degree curve (line). Alternatively, to get real time performance, simpler methods may be followed to determine some of the morphological classes of the ST segment. For example, to determine horizontal depression case, the deviation from the mean of a sample on the ST segment is restricted to a minimum threshold. In case of upsloping or downsloping depression case, the increasing and decreasing trend in the samples on the ST segment will suffice for the classification.

Finally, at block 144, the point of reference is determined based on the morphological classification of the ST segment. For example, the point of reference may be determined at a temporal distance of substantially 80 ms from said J-point, if the ST segment is classified as upsloping depression, convex depression or horizontal depression. If the ST segment is classified as downsloping depression, the J-point itself may be taken as the point of reference. On the other hand, if the ST segment is classified as elevation, the point of reference may be determined at a temporal distance of substantially 40 ms. The points of reference for the various morphologies are represented by the points 119A-119E on the ST segments 109A-109E respectively in FIGS. 9A-9E. Measurement of ST deviation from the points of reference determined as described above are particularly advantageous for accurate automated evaluation of the gradation of cardiac abnormalities, such as myocardial ischemia.

Figure 10:
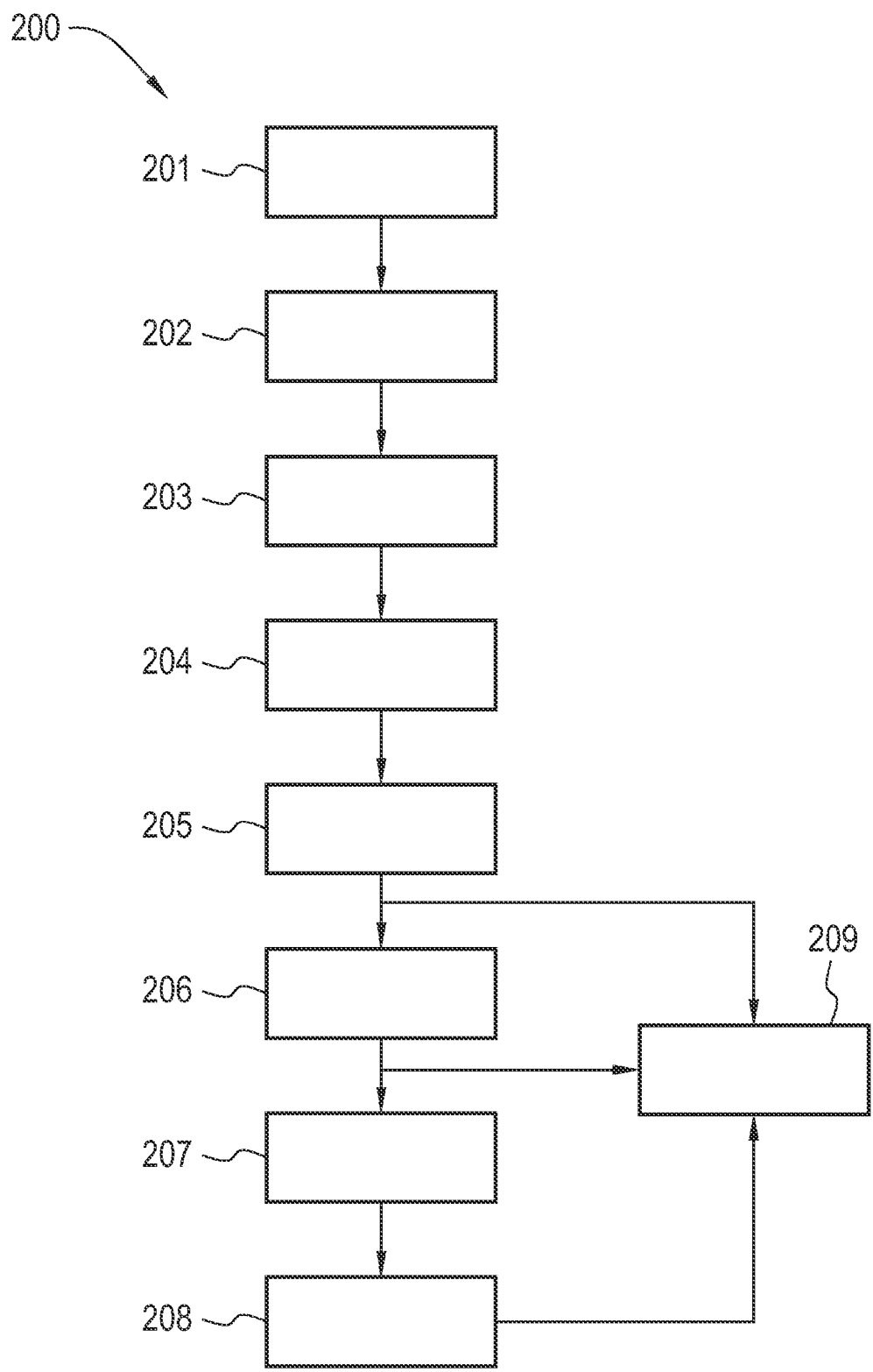
FIG. 10 is a flowchart illustrating an exemplary method for evaluating a medical condition of a patient from an ECG in accordance with the present invention.

FIG. 10 is a flowchart illustrating an exemplary method 200 for diagnosing a medical condition of a patient from an electrocardiogram. The method 200 includes providing digitized ECG data samples (block 201) and filtering the data samples (block 202). Block 203 involves adaptively determining a baseline for each heart beat cycle as described in detail above. The method further includes determining a J-point on the ST segment (block 204) and identifying a deviation of the J-point from the baseline (205). The deviation of the J-point from the baseline is an important clinical parameter and may be used to determine a cardiac abnormality (block 209), for example, a myocardial infarction, which is indicated as positive ST deviation (i.e., ST elevation). Large negative deviations of J-point from the baseline may also indicate an ischemic condition. At block 206, the ST segment is classified into an exact morphological class such as, for example, (a) upsloping depression, (b) convex depression, (c) horizontal depression, (d) downsloping depression and (e) elevation as described above. The result of the classification may also be used to determine a cardiac abnormality (block 209). Advantageously, in order to accurately diagnose a gradation of a cardiac abnormality, a point of reference is determined on the ST segment (block 207) that best characterizes the ST deviation. As described above, the point of reference may be determined as a function of a temporal distance from the J-point based on the classification of the ST segment. Subsequently the deviation of the point of reference from the baseline is determined (block 208) and a cardiac abnormality and/or a gradation thereof is diagnosed (block 209) based on the determined deviation of the point of reference from the baseline.

Although the invention has been described with reference to specific embodiments, this description is not meant to be construed in a limiting sense. Various modifications of the disclosed embodiments, as well as alternate embodiments of the invention, will become apparent to persons skilled in the art upon reference to the description of the invention. Accordingly, it is intended that the invention be limited only by the spirit and scope of the appended claims.

The invention claimed is:

1. A system for analyzing an electrocardiogram (ECG) signal, comprising:
an interface that receives an ECG waveform associated with a series of heart beat cycles of a patient, said ECG waveform comprising a P-wave, a QRS complex, a T-wave and an ST segment associated with heart electrical activity of the patient for each heart beat cycle; and
a signal processor that processes digitized data samples representing the ECG waveform to evaluate an ST segment deviation by:
determining a first and a second isoelectric portion of the ECG waveform, the first isoelectric portion lying temporally between a T-wave of a first heart beat cycle and a P-wave of a successive heart beat cycle, the second isoelectric portion lying temporally between a P-wave of the first heart beat cycle and a QRS complex of the first heart beat cycle,
determining a stability measure for each of said first and second isoelectric portions and adaptively selecting the first isoelectric portion or the second isoelectric portion as a baseline for the first heart beat cycle based on a comparison of the stability measures of said first and second isoelectric portions, and
determining a point of reference on an ST segment on the ECG waveform associated with the first heart beat cycle and evaluating a deviation of the determined point of reference on the ST segment from the selected baseline.

2. The system according to claim 1, wherein the signal processor determines the stability measures of said first and second isoelectric portions respectively based on a number of representative data samples for the first isoelectric portion and a number of representative data samples for the second isolecetric portion.

3. The system according to claim 1, wherein the signal processor adaptively selects successive baselines for said series of heart beat cycles.

4. The system according to claim 1, wherein the signal processor further determines an R-peak, a T-peak and a P-peak for each heart beat cycle, wherein the signal processor:
determines the T-peak of a heart beat cycle as a peak point in the ECG waveform between a temporal distance of 60 ms to 200 ms after the R-peak of that heart beat cycle, if a heart beat rate is greater than 120 beats per minute, and as a peak point in the ECG waveform between a temporal distance of 80 ms to 300 ms after the R-peak of that heart beat cycle, if the heart beat rate is lesser than or equal to 120 beats per minute, and
determines the P-peak a heart beat cycle as a peak point in the ECG waveform between a temporal distance of 60 ms to 160 ms before the R-peak of that heart beat cycle, if the heart beat rate is greater than 120 beats per minute, and as a peak point in the ECG waveform between a temporal distance of 80 m to 200 ms before said R-peak of that heart beat cycle, if the heart beat rate lesser than or equal to 120 beats per minute.

5. The system according to claim 1, wherein the signal processor determines the first isoelectric portion by:
determining exponential values of data samples of the digitized ECG waveform lying between a T-peak of the T-wave of said first heart beat cycle and a P-peak of the P-wave of the successive heart beat cycle,
identifying a series of data samples having a derivative of the determined exponential values below a predetermined threshold value, and
determining the first isoelectric portion as a portion of the ECG waveform represented by the identified series of data samples.

6. The system according to claim 1, further comprising a signal preprocessor that filters the digitized ECG waveform from said interface and transmits the filtered digitized ECG waveform to the signal processor for further processing.

7. The system according to claim 1, wherein the signal processor identifies a J-point on said ST segment and determines said J-point as said point of reference.

8. The system according to claim 1, wherein the signal processor identifies a J-point on said ST segment and determines said point of reference at a predetermined temporal distance from said J-point, wherein said pre-determined temporal distance is obtained based upon a classification of said ST segment into one of a plurality of predetermined morphological classes.

9. The system according to claim 8, wherein the signal processor classifies said ST segment into one of said plurality of predetermined morphological classes including an upsloping depression, a convex depression, a horizontal depression, a downsloping depression and an elevation.

10. The system according to claim 9, wherein the signal processor:
determines the point of reference at a temporal distance of substantially 80 ms from said J-point, if the ST segment is classified as upsloping depression,
determines the point of reference at a temporal distance of substantially 80 ms from said J-point, if the ST segment is classified as convex depression,
determines the point of reference at a temporal distance of substantially 80 ms from said J-point, if the ST segment is classified as horizontal depression,
determines the point of reference as the J-point, if the ST segment is classified as downsloping depression, and
determines the point of reference at a temporal distance of substantially 40 ms from said J-point, if the ST segment is classified as elevation.

11. The system according to claim 9, wherein the signal processor classifies said ST segment as depression or elevation by determining a deviation of said J-point from said baseline.

12. The system according to claim 1, further comprising a diagnostic module that evaluates a medical condition of the patient based on the deviation of the point of reference from the selected baseline value.

13. A method for analyzing an electrocardiogram (ECG) signal, comprising:
providing digitized data samples of an ECG waveform associated with a plurality of heart beat cycles of a patient, said ECG waveform comprising a P-wave, a QRS complex, a T-wave and an ST segment associated with heart electrical activity of the patient for each heart beat cycle;
determining a first isoelectric portion of said ECG waveform from data samples of said ECG waveform between a T-wave of a first heart beat cycle and a P-wave of a successive heart beat cycle and a second isoelectric portion of said ECG waveform from data samples of said ECG signal waveform between P-wave of the first heart beat cycle and a QRS complex of the first heart beat cycle;
determining a stability measure for each of said first and second isoelectric portions and adaptively selecting the first isoelectric portion or the second isoelectric portion as a baseline for the first heart beat cycle based on a comparison of the stability measures of said first and second isoelectric portions;
determining a point of reference on an ST segment of the ECG waveform associated with the first heart beat cycle; and evaluating a deviation of the point of reference with respect to the selected baseline.

14. The method according to claim 13, further comprising filtering the provided digitized ECG waveform.

15. The method according to claim 13, comprising determining the stability measures of said first and second isoelectric portions respectively based on a number of representative data samples for the first isoelectric portion and a number of representative data samples for the second isolecetric portion.

16. A method for aiding diagnosis of a medical condition of a patient from an electrocardiogram (ECG) signal, comprising:
providing digitized data samples of an ECG waveform associated with a plurality of heart beat cycles of the patient, said ECG waveform comprising a P-wave, a QRS complex, a T-wave and an ST segment associated with heart electrical activity of the patient for each heart beat cycle;
adaptively selecting a baseline for a first heart beat cycle between a first isoelectric portion of said ECG waveform lying temporally between a T-wave of the first heart beat cycle and a P-wave of a successive heart beat cycle and a second isoelectric portion lying temporally between P-wave of the first heart beat cycle and a QRS complex of the first heart beat cycle, said adaptive selection being based on a stability measure determined for each of said first and second isoelectric portions;
evaluating a deviation of a J-point on an ST segment associated with the first heart beat cycle with respect to the selected baseline; and
classifying the ST segment into one of a plurality of morphological classes based on the determined deviation of the J-point from the selected baseline.

17. The method according to claim 16, wherein classifying the ST segment comprises classifying said ST segment into one of said plurality of predetermined morphological classes including an upsloping depression, a convex depression, a horizontal depression, a downsloping depression and an elevation.

18. The method according to claim 16, further comprising:
determining a point of reference on the ST segment based on said classification; and
evaluating a medical condition of the patient based on a deviation of the point of reference from said selected baseline.

19. The method according to claim 18, wherein determining said point of reference further comprises:
determining the point of reference at a temporal distance of substantially 80 ms from said J-point, if the ST segment is classified as upsloping depression;
determining the point of reference at a temporal distance of substantially 80 ms from said J-point, if the ST segment is classified as convex depression;
determining the point of reference at a temporal distance of substantially 80 ms from said J-point, if the ST segment is classified as horizontal depression;
determining the point of reference as the J-point, if the ST segment is classified as downsloping depression; and
determining the point of reference at a temporal distance of substantially 40 ms from said J-point, if the ST segment is classified as elevation.

20. The method according to claim 18, wherein evaluating the medical condition of the patient comprises evaluating a gradation of myocardial ischemia.

* * * * *